United States Patent
Scharich, III et al.

(10) Patent No.: US 11,559,422 B2
(45) Date of Patent: Jan. 24, 2023

(54) URINE COLLECTION SYSTEM FOR USE ON PATIENT SUPPORT APPARATUS

(71) Applicant: Stryker Corporation, Kalamazoo, MI (US)

(72) Inventors: David Scharich, III, Coloma, MI (US); Matthew A. Cutler, Portage, MI (US); Anish Paul, Kalamazoo, MI (US); Steven L. Birman, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 706 days.

(21) Appl. No.: 16/418,134

(22) Filed: May 21, 2019

(65) Prior Publication Data
US 2019/0358075 A1 Nov. 28, 2019

Related U.S. Application Data

(60) Provisional application No. 62/674,884, filed on May 22, 2018.

(51) Int. Cl.
*A61G 7/02* (2006.01)
*A61F 5/44* (2006.01)
*A61M 25/00* (2006.01)

(52) U.S. Cl.
CPC .............. *A61F 5/4404* (2013.01); *A61G 7/02* (2013.01); *A61M 25/0017* (2013.01)

(58) Field of Classification Search
CPC .......... A61F 5/4404; A61F 5/44; A61F 5/451; A61G 7/02; A61G 7/0503; A61G 5/1002; A61G 9/006; A61G 9/00; A61M 25/0017; A61M 1/70; A61B 10/007; A61B 5/208
See application file for complete search history.

(56) References Cited

U.S. PATENT DOCUMENTS

| | | | | |
|---|---|---|---|---|
| 4,448,207 A | * | 5/1984 | Parrish | G01F 23/2962 600/584 |
| 4,658,834 A | * | 4/1987 | Blankenship | G01F 23/2968 600/584 |
| 5,891,051 A | * | 4/1999 | Han | A61B 5/208 600/580 |
| 7,621,898 B2 | | 11/2009 | Lalomia et al. | |
| 7,722,584 B2 | * | 5/2010 | Tanaka | A61F 5/451 604/326 |

(Continued)

FOREIGN PATENT DOCUMENTS

| | | |
|---|---|---|
| AU | 2011232780 A1 | 4/2012 |
| CN | 103735344 A | 4/2014 |

OTHER PUBLICATIONS

English language abstract and machine-assisted English translation for CN 103735344 extracted from espacenet.com database on Jun. 10, 2019, 12 pages.

(Continued)

*Primary Examiner* — Erich G Herbermann
*Assistant Examiner* — Alessandro R Del Priore
(74) *Attorney, Agent, or Firm* — Howard & Howard Attorneys PLC (57) ABSTRACT

A urine collection system is provided for use on a patient support apparatus. The urine collection system comprises a housing and a container for mounting to the housing in a releasable manner.

16 Claims, 10 Drawing Sheets

(56) References Cited

U.S. PATENT DOCUMENTS

| | | | |
|---|---|---|---|
| 9,074,920 B2 | 7/2015 | Mendels et al. | |
| 2007/0106177 A1* | 5/2007 | Hama | A61M 1/70 |
| | | | 600/573 |
| 2007/0225668 A1* | 9/2007 | Otto | A61G 9/006 |
| | | | 604/347 |
| 2011/0092890 A1 | 4/2011 | Stryker et al. | |
| 2011/0113562 A1* | 5/2011 | Uzzle | A61G 7/0506 |
| | | | 5/503.1 |
| 2014/0090173 A1 | 4/2014 | DiMaio et al. | |
| 2014/0316380 A1* | 10/2014 | Davis | A61M 25/00 |
| | | | 604/523 |

OTHER PUBLICATIONS

Buck and Buck, "Drainage Bag Cover by Adaptable Designs Webpage", https://www.buckandbuck.com/accessories/wheelchair-accessories/urinary-drainage-bag.html, 2018, 2 pages.

* cited by examiner

URINE COLLECTION SYSTEM FOR USE ON PATIENT SUPPORT APPARATUS

RELATED APPLICATION

This application claims priority to and the benefit of U.S. Provisional Patent Application No. 62/674,884, filed on May 22, 2018, which is hereby incorporated herein by reference.

BACKGROUND

A Foley catheter is a flexible tube that is inserted into a patient's bladder to drain urine from the bladder. The tube is connected to a bag so that the urine drains from the patient's bladder into the bag. Often, the bags comprise thin, flexible walls so that the bags take up little space before use, but are able to easily expand when being filled. During use, the bag is typically attached to a patient support apparatus via one or more hangers so that a caregiver can replace the bag when full. In order for the bag to easily collect urine from the patient's bladder, the bag is located at an elevation below the patient's bladder so that gravity draws the urine into the bag. This usually means that the bag hangs off a support frame of the patient support apparatus below a patient support surface. Sometimes, the patient support apparatus is configured to assume a low height configuration in which the patient support surface is near a floor surface. As a result, owing to the bag being hung below the patient support surface, there is a risk for the bag to drag along the floor surface during transport, which could damage the bag and possibly compromise the bag (e.g., tear it) and release its contents onto the floor surface.

A urine collection system is desired that addresses one or more of the aforementioned challenges.

DETAILED DESCRIPTION

Figure 1:
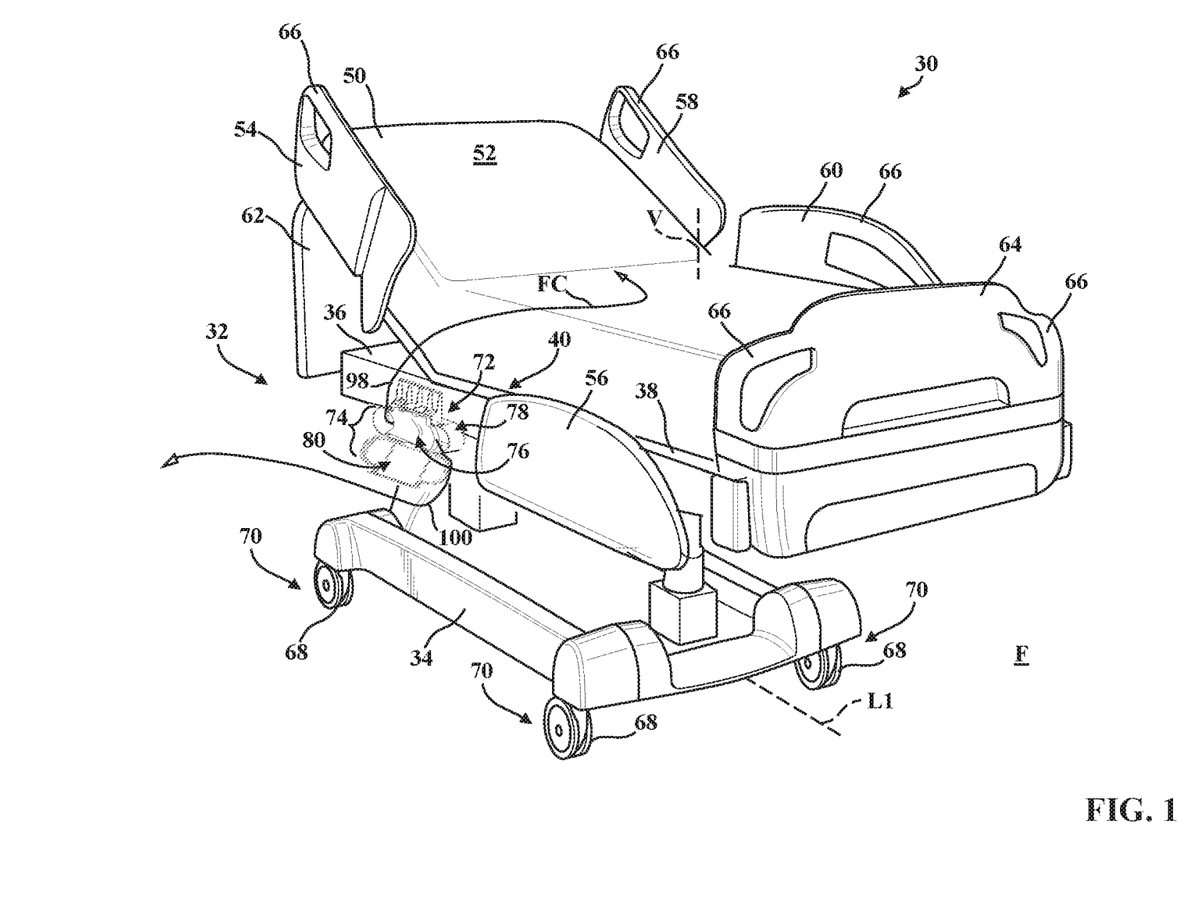
FIG. 1 is a perspective view of a patient support apparatus with a urine collection system.

Referring to FIG. 1, a patient support apparatus 30 is shown for supporting a patient in a health care setting. The patient support apparatus 30 illustrated in FIG. 1 comprises a hospital bed. In other embodiments, however, the patient support apparatus 30 may comprise a stretcher, cot, wheelchair, chair, or similar apparatus utilized in the care of a patient.

A support structure 32 provides support for the patient. The support structure 32 illustrated in FIG. 1 comprises a base 34 and a support frame 36 disposed above the base 34 and supported by the base 34. The support structure 32 also comprises a patient support deck 38 disposed on the support frame 36. The patient support deck 38 comprises sections, some of which are capable of articulating (e.g., pivoting) relative to the support frame 36. The patient support deck 38 provides a patient support surface 40, upon which the patient is supported.

A mattress 50 is disposed on the patient support deck 38 during use. The mattress 50 comprises a secondary patient support surface 52 upon which the patient is supported. The mattress 50 may be omitted in certain embodiments, such that the patient rests directly on the patient support surface 40. The base 34, support frame 36, patient support deck 38, and patient support surfaces 40, 52, each comprise a head end and a foot end corresponding to designated placement of the patient's head and feet on the patient support apparatus 30. The base 34 comprises a longitudinal axis L1 along its length from the head end to the foot end. The base 34 also comprises a vertical axis V arranged crosswise (e.g., perpendicularly) to the longitudinal axis L1 along which the support frame 36 is lifted and lowered relative to the base 34. The construction of the support structure 32 may take on any known or conventional design, and is not limited to that specifically set forth above.

Patient barriers, such as side rails 54, 56, 58, 60 are coupled to the support frame 36 and/or patient support deck 38 and are thereby supported by the base 34. If the patient support apparatus 30 is a stretcher or a cot, there may be fewer side rails.

A headboard 62 and a footboard 64 are coupled to the support frame 36. The headboard 62 and footboard 64 may be coupled to any location on the patient support apparatus 30, such as the support frame 36 or the base 34.

Caregiver interfaces 66, such as handles, are shown integrated into the footboard 64 to facilitate movement of the patient support apparatus 30 over a floor surface F. Additional caregiver interfaces 66 may be integrated into other components of the patient support apparatus 30, such as the headboard 62 or the side rails 54, 56, 58, 60. The caregiver interfaces 66 are graspable by the caregiver to manipulate the patient support apparatus 30 for movement, and the like. Other forms of the caregiver interface 66 are also contemplated.

Wheels 68 are coupled to the base 34 to facilitate transport over the floor surface F. The wheels 68 are arranged in each of four quadrants of the base 34 adjacent to corners of the base 34. In the embodiment shown, the wheels 68 are caster wheels able to rotate and swivel relative to the support structure 32 during transport. Each of the wheels 68 forms part of a caster assembly 70. Each caster assembly 70 is mounted to the base 34. Additional wheels are also contemplated. For example, the patient support apparatus 30 may comprise four non-powered caster wheels 68, along with one or more powered wheels. It should be appreciated that although the caster assembly 70 is shown and described as being part of the patient support apparatus 30, the caster assembly 70 could be used with any mobility apparatus in which caster wheels are suitable for providing mobility.

A urine collection system 72 is shown attached to the patient support apparatus 30. The urine collection system 72 comprises a housing 74 and a urine collection container 76. The container 76 is used to collect urine from the patient, such as by connecting the container 76 to a foley catheter FC. The housing 74 is provided to at least partially support and/or protect the container 76 from damage, from view, or the like. The container 76 is configured in some embodiments to be removably coupled to the housing 74.

The housing 74 may be coupled to the patient support apparatus 30 by one or more fasteners, hangers, snap-fit connections, or the like. In other versions, the housing 74 may be integral with the patient support apparatus 30. The housing 74 may be configured to fully enclose the container 76 therein or may only partially enclose the container 76. The housing 74 may be configured to completely seal the container 76 therein so that if liquid spills from the container 76 the liquid is contained within the housing 74 until removed.

In the embodiment shown in FIG. 1, the housing 74 comprises a housing base 78 mounted to the support frame 36 and a housing lid 80 movable relative to the housing base 78. The housing base 78 may be attached at any suitable location on the patient support apparatus 30, including any portion of the support structure 32, on the headboard 62, the footboard 64, on any of the side rails 54, 56, 58, 60, or any location in which the urine collection system 72 can operate to drain urine from a patient disposed on the patient support surfaces 40, 52, including on the mattress 50. In each case, the housing base 78 is carried by the support structure 32, even though it may be mounted directly to one of the side rails 54, 56, 58, 60, headboard 62, footboard 64, mattress 50, or the like.

Figures 2, 2A:
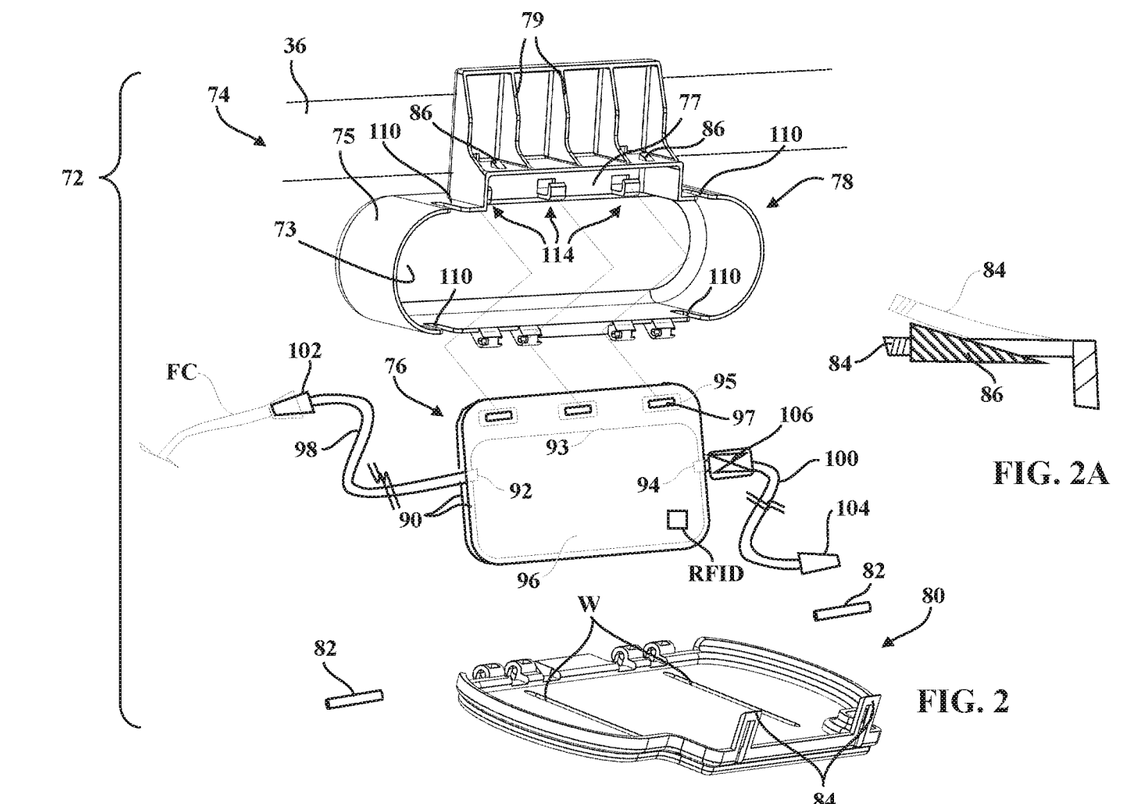
FIG. 2 is an exploded perspective view of the urine collection system comprising a housing and container.
FIG. 2A is a cross-sectional view illustrating a latch engaging a catch to close the housing.

Referring to FIG. 2, the housing base 78 comprises a bottom wall 73, one or more peripheral walls 75 extending upwardly from the bottom wall 73 to a rim, and an intermediate wall 77. Any number of walls suitable to form a container support structure for the container 76 and/or to protect the container 76 may be employed. Ribs 79 are also provided to reinforce a mounting portion of the housing base 78, which is mounted to the support frame 36. In the version shown, the bottom wall 73 is arranged vertically in the direction of the vertical axis V (see FIG. 1) and the peripheral wall 75 extends laterally from the support structure 32 so that the housing base 78 has a side opening that opens to the side of the patient support apparatus 30.

In one embodiment, the housing lid 80 is pivotally connected to the housing base 78 via one or more pivot elements, such as pivot pins 82. The housing base 78 and the housing lid 80 may have one or more hinge portions to receive the pivot pins 82 and form a hinge of the housing 74. The housing lid 80 comprises one or more snap-fit latches 84 that engage corresponding catches 86 of the housing base 78 when the housing lid 80 is pivoted to a closed configuration. The latches 84 are resiliently biased toward a latched position so that the latches 84 releasably lock the housing lid 80 to the housing base 78 when the latches 84 engage the catches 86, as shown in FIG. 2A. The latches 84 can be released when a caregiver applies a force to the latches 84 to flex the latches 84 away from their latched positions, away from the catches 86 (see hidden lines in FIG. 2A). Any suitable closure elements can be employed to releasably lock the housing lid 80 to the housing base 78. The housing base 78 may be oriented and attached to the patient support apparatus 30 as shown so that the housing lid 80 falls open under gravity when the latches 84 are released to reveal the side opening into the housing base 78.

In the closed configuration, the housing base 78 and housing lid 80 provide a storage space. The housing base 78 and the housing lid 80 may be configured to fully enclose the container 76 in the storage space or may at least partially enclose the container 76 in the storage space in the closed configuration. In some versions, when the housing lid 80 is in the closed configuration, the container 76 may be sealed therein so that if liquid spills from the container 76 the liquid remains contained within the housing 74 until removed. In some versions, the housing base 78 may be oriented so that the housing base 78 acts as a secondary container for the liquid stored in the container 76 in case of leakage from the container 76. In some versions, the housing 74 may comprise a housing base without any housing lid—in this case, the housing base is considered the housing. In further versions, the housing 74 itself may serve as the container 76 for the urine to be collected from the patient.

In some embodiments, the housing 74 may comprise a first material. The housing 74, which may include the housing base 78 and/or the housing lid 80, may comprise, consist essentially of, or consist of, the first material, which may be a polymer, metal, combinations thereof, or any other suitable materials. The housing 74 (e.g., the housing base 78 and/or the housing lid 80) may be formed of transparent or translucent materials so that the container 76 is visible through the housing 74. Other materials are also contemplated. The first material may be selected from elastomers, thermoplastic elastomers, thermoplastics, and combinations thereof. The housing 74 may be more rigid that the container 76 when tested in accordance with ASTM D2240, Standard Test Method for Rubber Property—Durometer Hardness.

Various non-limiting examples of suitable thermoplastics and thermoplastic elastomers include polyolefins, polyolefin elastomers, polyvinylchlorides (PVC), polyamides (PA), styrenic elastomers, thermoplastic vulcanate elastomer (TPV), fluoropolymers, silicones, polyesters, polyoxymethylenes (POM), polyurethane, thermoplastic polyurethanes (TPU), and combinations thereof. For example, in one specific embodiment, the first material comprises thermoplastic polyurethane, polyoxymethylene, polyalkylene terephthalate, and combinations thereof. By way of a non-limiting example, the first material comprises polyurethane or a thermoplastic polyurethane (TPU). The first material in another non-limiting example, may comprise nylon, such as nylon 66. The housing base 78 and/or the housing lid 80 may have a preformed shape and the walls of the housing base 78 and/or the housing 80 may be rigid such that they substantially maintain the preformed shape when the container 76 is being filled.

Figure 3:
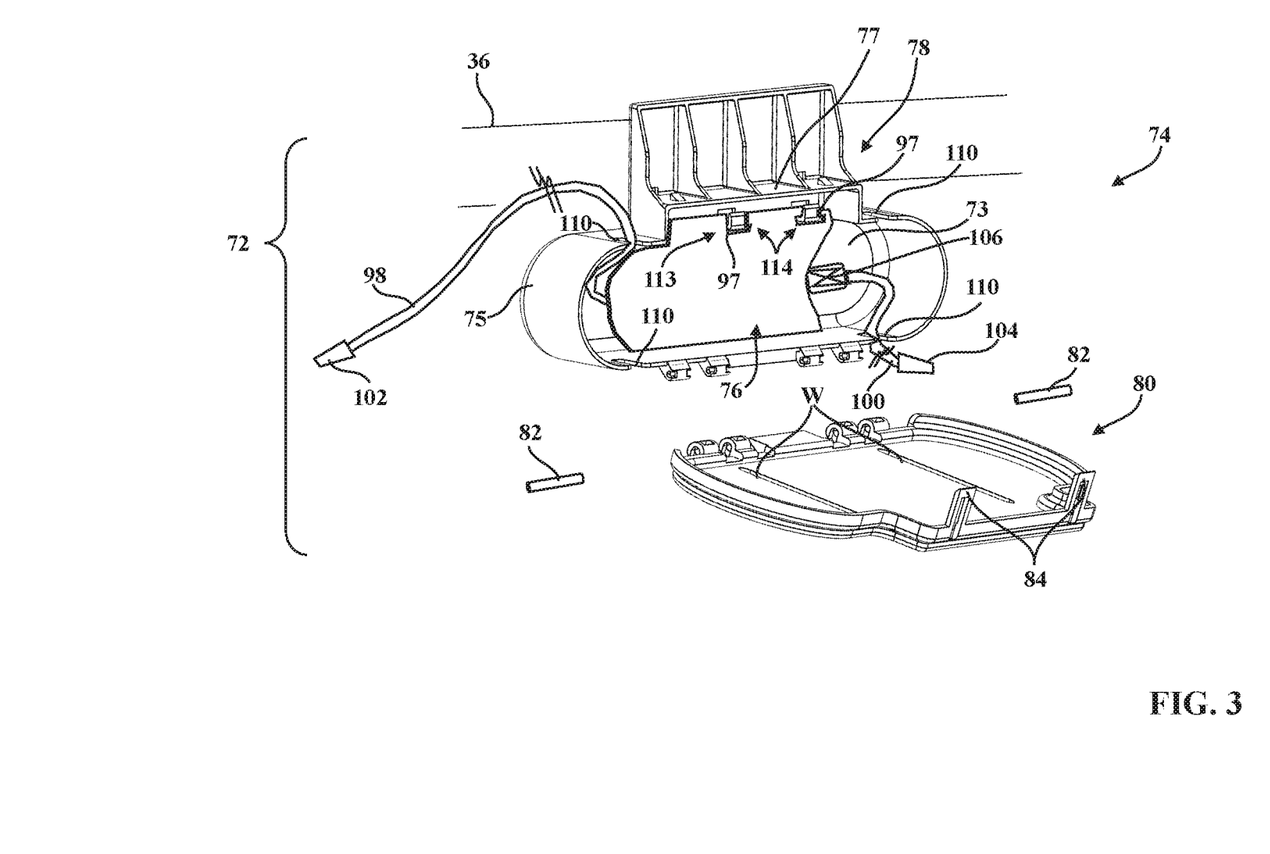
FIG. 3 is a perspective view of the urine collection system illustrating the container coupled to the housing.

Referring to FIGS. 2 and 3, the container 76 comprises a pair of flexible walls 90 sealed and connected together about their peripheries to form an inlet opening 92, an outlet opening 94, and a collection chamber 96 therebetween. The walls 90 may be sealed and connected together via radio frequency welding, ultrasonic welding, adhesive, or the like. For example, the walls 90 may be welded together along weld lines 93 to form the inlet opening 92, the outlet opening 94, and the collection chamber 96. The walls 90 may also be welded together along weld lines 95 surrounding openings 97 formed through the walls 90 (three are shown, but there may be more or less). The walls 90 are flexible so that the container 76 may be expandable when being filled with liquid. In some cases, the walls 90 may be elastic and capable of stretching, or the walls 90 may be generally inelastic such that they do not substantially stretch when expanding. In this embodiment, the walls 90 are configured to form a bag that may be capable of storing 1000 to 3000 milliliters of liquid, 1500 to 2500 milliliters of liquid, or the like.

The walls 90 may comprise a second material that is softer and more flexible than the first material forming the housing 74. The walls 90 comprise, consist essentially of, or consist of, the second material, which may be a polymer. In many embodiments, the second material is selected from elastomers, thermoplastic elastomers, thermoplastics, and combinations thereof. Other second materials are also contemplated. In one non-limiting example, the walls 90 may be formed of vinyl material.

In embodiments where the first material is harder than the second material, the first material can have a Shore A hardness which is a hardness greater than about 2, about 4, about 6, about 8, about 10, about 12, about 14, about 16, about 18, about 20, about 22, about 24, about 26, about 28, or about 30, durometer units than the hardness of the second material, when tested in accordance with ASTM D2240, Standard Test Method for Rubber Property—Durometer Hardness. Similarly, the first material may be better measured using a Shore D scale by virtue of being substantially harder than the second material. The first material may form a rigid housing and may have a Shore D hardness of at least 20, at least 40, at least 60 and/or a Shore D hardness of from about 20 to about 120, or from about 40 to about 110, or from about 60 to about 95, when tested in accordance with ASTM D2240, Standard Test Method for Rubber Property—Durometer Hardness.

An inlet tube 98 is coupled to the container 76. The inlet tube 98 has a first end portion located in the inlet opening 92 to provide a drainage pathway from the Foley catheter FC to the collection chamber 96. The inlet tube 98 is attached to the walls 90 (between the walls 90) so that urine from the patient is collected in the collection chamber 96. Sealant, adhesive, welding, or the like may be used to seal between the inlet tube 98 and the walls 90 to prevent any leakage of liquid around the inlet tube 98 and outside of the collection chamber 96. In some versions, the inlet tube 98 may be integrally formed with the walls 90 and thereby coupled to the container 76 by virtue of being integrally formed with the container 76.

An outlet tube 100 is coupled to the container 76. The outlet tube 100 has a first end portion located in the outlet opening 94 to provide a disposal pathway from the collection chamber 96 to a final disposal location, such as a waste drain, waste collection unit, or the like. For instance, the outlet tube 100 may be configured to connect to the waste collection unit disclosed in U.S. Pat. No. 7,621,898 to Lalomia et al., filed on Dec. 14, 2005, entitled "Medical/surgical Waste Collection Unit Including Waste Containers of Different Storage Volumes with Inter-container Transfer Valve and Independently Controlled Vacuum Levels," hereby incorporated herein by reference. The outlet tube 100 is attached to the walls 90 (between the walls 90). Sealant, adhesive, welding, or the like may be used to seal between the outlet tube 100 and the walls 90 to prevent any leakage of liquid around the outlet tube 100 and outside of the collection chamber 96. In some versions, the outlet tube 100 may be integrally formed with the walls 90 and thereby coupled to the container 76 by virtue of being integrally formed with the container 76. In some versions, the container 76 lacks the outlet opening 94, such that there is only a single opening into the container 76, which can operate merely as an inlet or as an inlet/outlet. In this case, there is no dedicated outlet tube 100.

A connector 102 may be attached to a second end portion of the inlet tube 98 to connect the inlet tube 98 to the Foley catheter FC or the like that is placed into the patient's bladder. A second connector 104 may be attached to a second end portion of the outlet tube 100.

A stop valve 106, such as a stop cock, may be coupled to the outlet tube 100 to selectively shut off flow through the outlet tube 100. During use, the stop valve 106 may be closed to prevent flow of liquid from the collection chamber 96 through the outlet tube 100, but the outlet tube 100 may be opened to drain liquid from the collection chamber 96 once full. In some cases, the stop valve 106 may be open during use to drain to a disposal location.

Figure 3A:
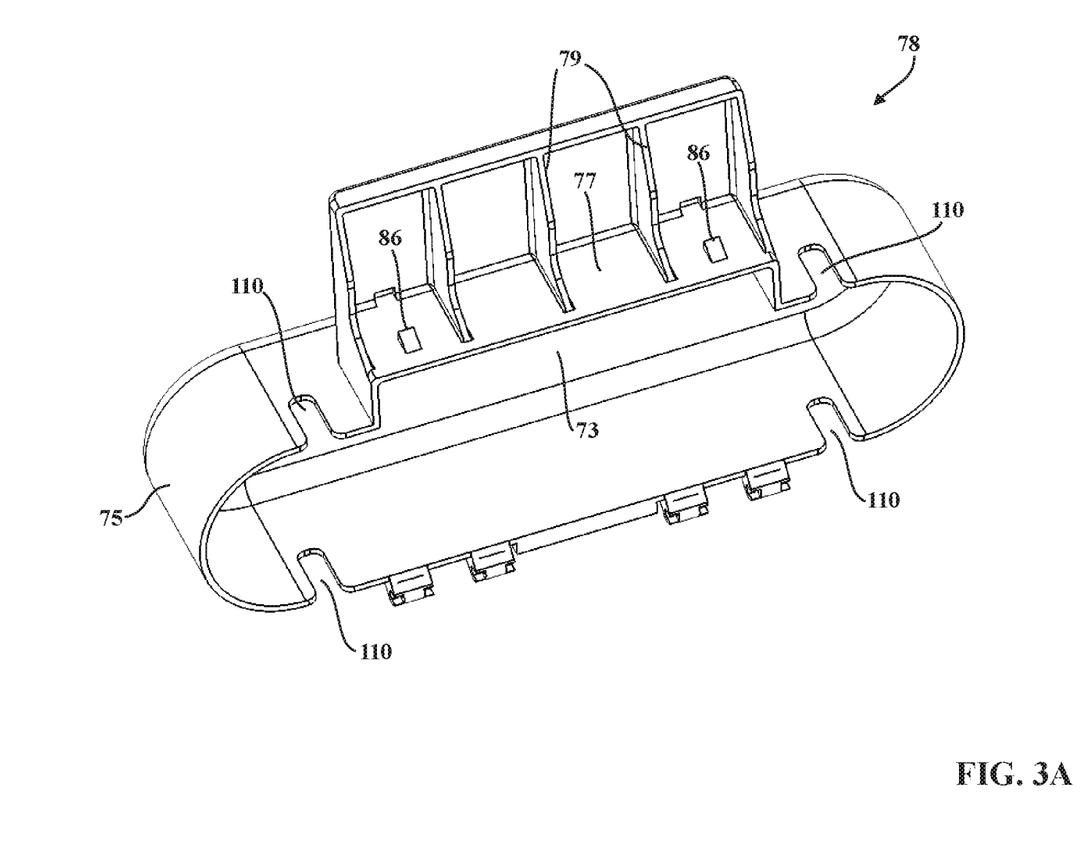
FIG. 3A is a perspective view of a housing base.
Figure 3B:
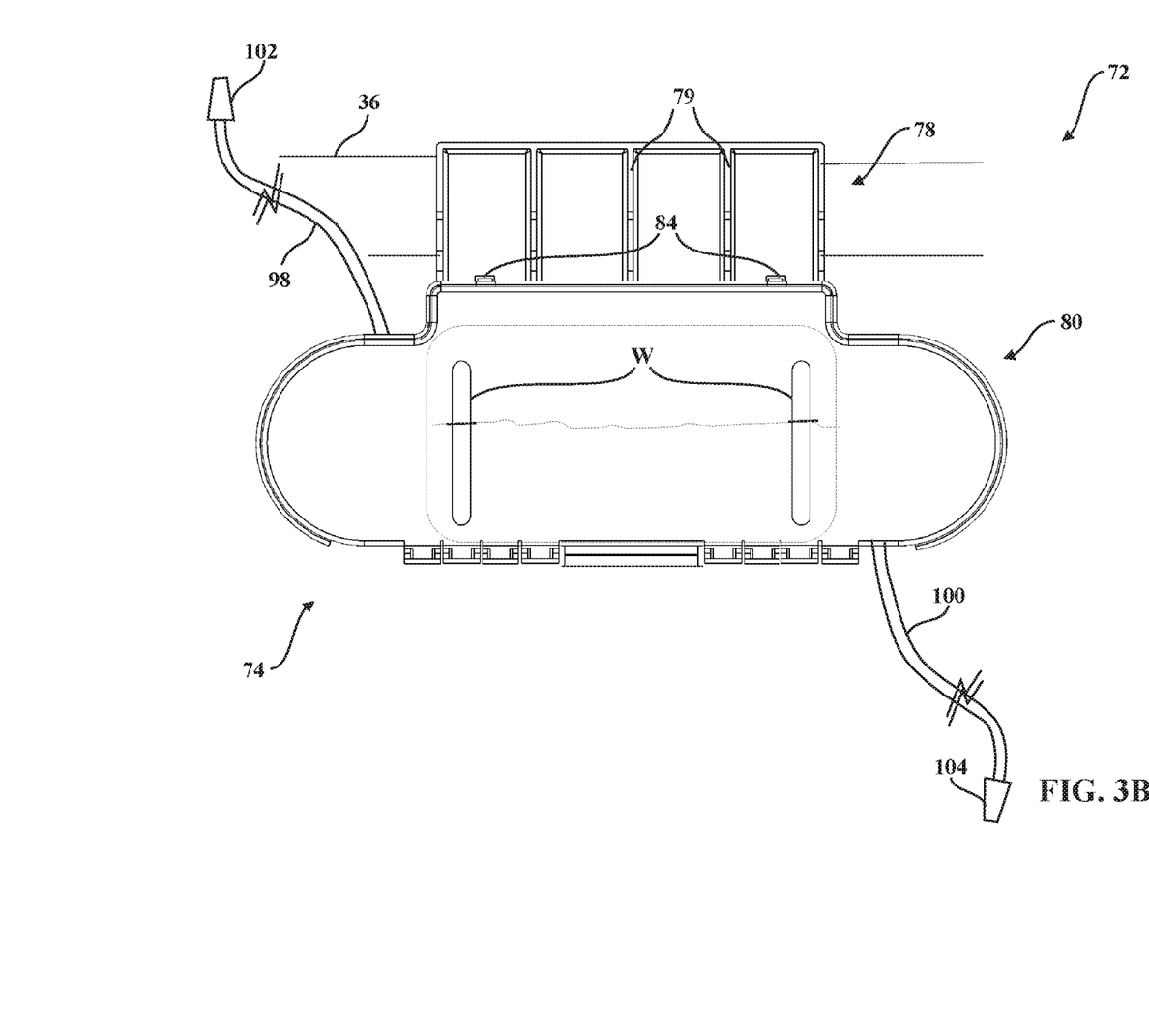
FIG. 3B is a front view of the urine collection system.

Referring to FIGS. 3, 3A, and 3B, the housing 74 may comprise one or more line managers to organize the inlet tube 98 and the outlet tube 100. In the version shown, the line managers comprise openings 110 formed in the peripheral wall 75 of the housing base 78. The openings 110 are sized to be slightly larger than the tubes 98, 100 to easily route the tubes 98, 100 from inside the housing 74 to outside the housing 74 (while the container 76 remains inside the housing 74). The openings 110 may be notches, slots, throughbores, or the like. Other line managers are also contemplated such as clips and the like. The line managers may be integral with the housing base 78 and/or the housing lid 80, or may be separate components. One or more window openings W may be defined through the housing lid 80 (see FIG. 3B) and/or the housing base 78 to visually determine when the container 76 is full and ready to removed and replaced with a new container 76. The window openings W may be placed at any suitable location on the housing 74, and may be absent in some embodiments. The window openings W may be covered in some cases, such as with transparent or translucent material, such as when the housing 74 is configured to fully seal and/or fully enclose the container 76 therein.

Figure 4:
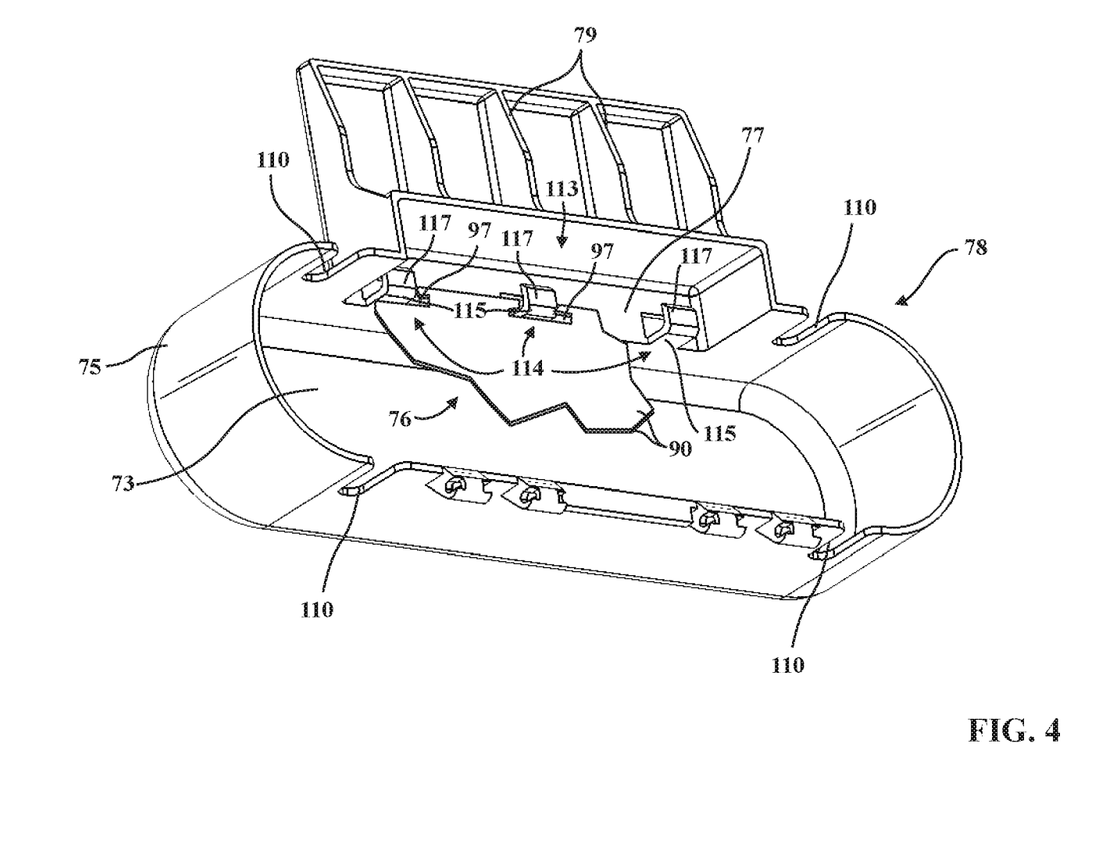
FIG. 4 is another perspective view of the housing base illustrating coupling of the container to the housing base.

Referring to FIG. 4, a releasable coupling mechanism 113 is provided to releasably couple the container 76 to the housing 74. The releasable coupling mechanism comprises first couplers and second couplers that interact to secure the container 76 to the housing 74. Only a fragmented portion of the container 76 is shown in FIG. 4 to illustrate how the container 76 may be releasably coupled to the housing 74. In the version shown, the first couplers comprise retainers 114 provided on the housing base 78 and the second couplers comprise the openings 97 in the container 76 so that the container 76 is able to hang by the retainers 114 inside the housing 74.

The retainers 114 support the container 76 during use. Each of the retainers 114 comprises a leg 115 attached to the intermediate wall 77 of the housing base 76. The legs 115 extend from the intermediate wall 77 to fingers 117. The fingers 117 are spaced from the intermediate wall 77 of the housing base 78 so that a gap exists between the fingers 117 and the intermediate wall 77. Thus, in the version shown, the retainers 114 comprise hooks.

The retainers 114 may be formed separately from the housing base 78 or may be integrally formed with the housing base 78. The openings 97 are sized to receive the retainers 114 so that the container 76 can be fitted onto the retainers 114 by locating the container 76 over the retainers 114 until part of the container 76 surrounding the openings 97 is supported on the legs 115. The retainers 114 and the openings 97 are one example of first and second couplers of a releasable coupling mechanism acting to releasably couple the housing 74 and the container 76. Other types of releasable coupling mechanisms are also contemplated, such as snap-fit connectors, hook and loop connectors, releasable adhesive tape, and the like, and the releasable coupling mechanisms can be placed at any suitable location for releasable coupling.

Figure 5:
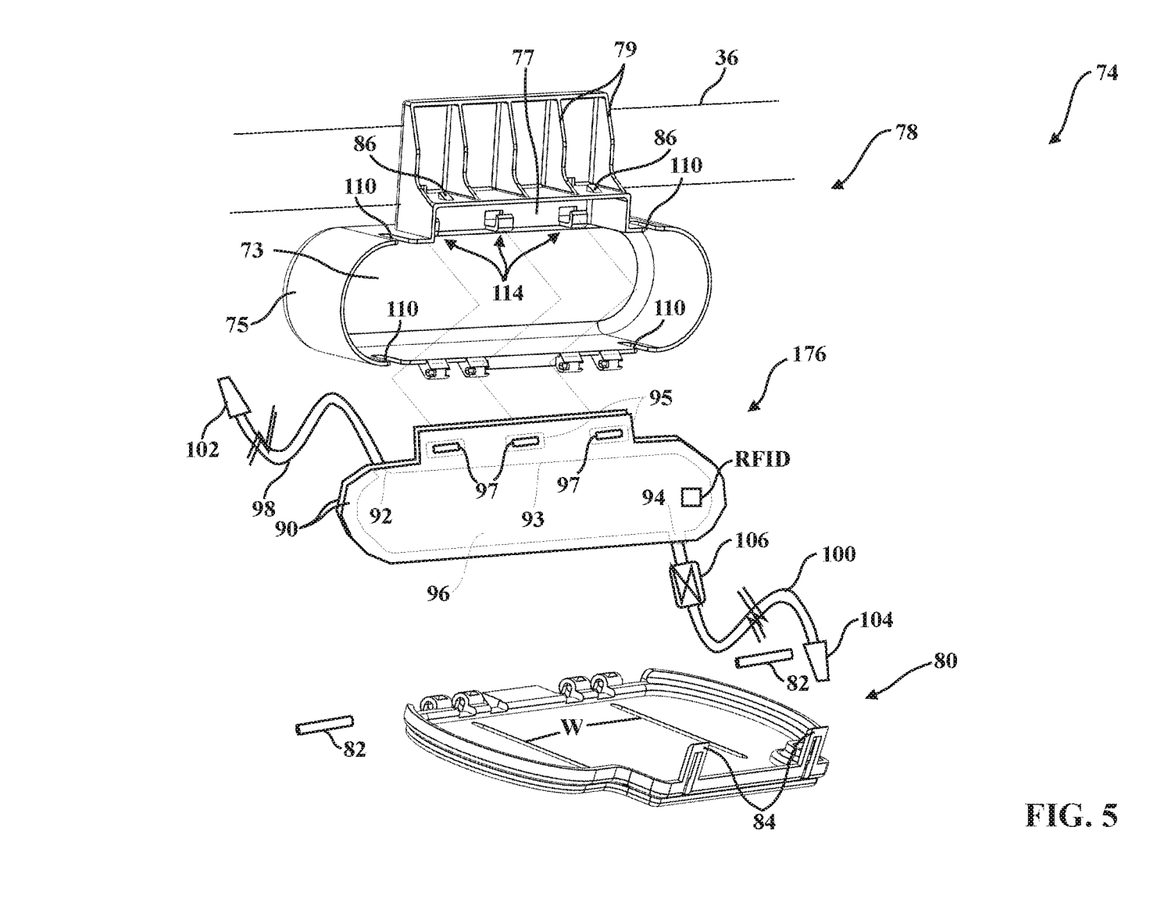
FIG. 5 is an exploded view of the urine collection system with an alternative container.

An alternative container 176 is shown in FIG. 5. This container 176 comprises the same features as the container 76 previously described except that the container 176 has a shape that is generally congruent with a shape of the housing base 78 so that the container 76 takes up a substantial amount of interior space formed by the bottom wall 173 and the peripheral walls 175 of the housing base 78.

Figure 6:
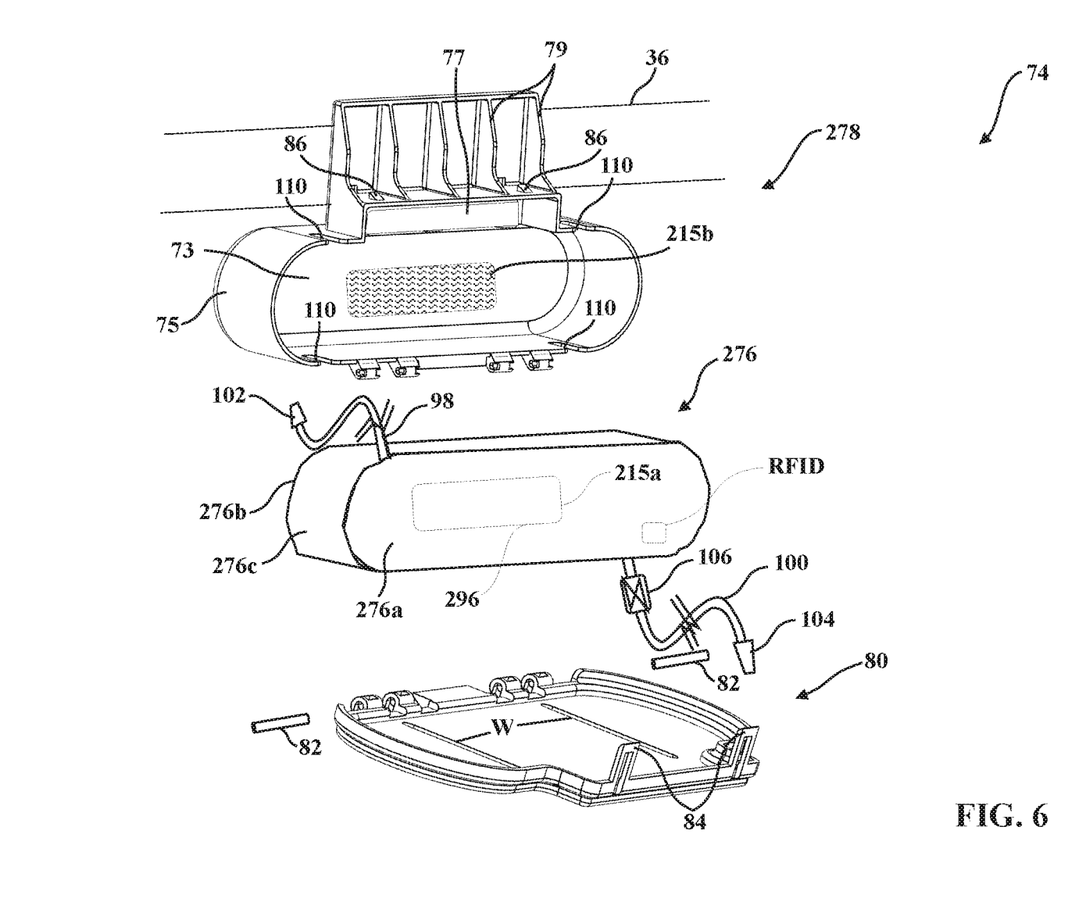
FIG. 6 is an exploded view of the urine collection system with another alternative container.

Referring to FIG. 6, another alternative container 276 is shown. In this version, the container 276 is more rigid than the containers 76, 176. The container 276 has a top wall 276a, a bottom wall 276b, and at least one peripheral wall 276c to define the collection chamber 296. The tubes 98, 100 are connected to one or more of the walls 276a, 276b, 276c in a liquid tight manner so that the urine can be collected in the collection chamber 296 and disposed of when appropriate, as previously described. The walls may be formed of the first material used to form the housing 74 or may be formed of a material that is at least harder than the second material, but may be softer than the first material, e.g., semi-rigid. In one version, the container 276 may be formed of blow-molded high density polyethylene, similar to a milk jug.

The container 276 may have a preformed shape and, unlike the containers 76, 176, is not configured to substantially expand in any dimension when being filled with liquid such that the container 276 substantially maintains the preformed shape when filled. The container 276 may be shaped to mate with the housing base 78 and may be held within the housing base 278 by a releasable coupling mechanism such as releasable adhesive tape, hook and loop fasteners, and the like. For example, hook and loop fasteners 215a, 215b may be employed with a hook portion 215a coupled to a bottom of the container 276 and a loop portion 215b coupled to the bottom wall 73 of the housing base 278. In this version, the hook and loop fasteners 215a, 215b are another example of first and second couplers that engage one another to secure the container 276 in the housing 74.

Figure 7:
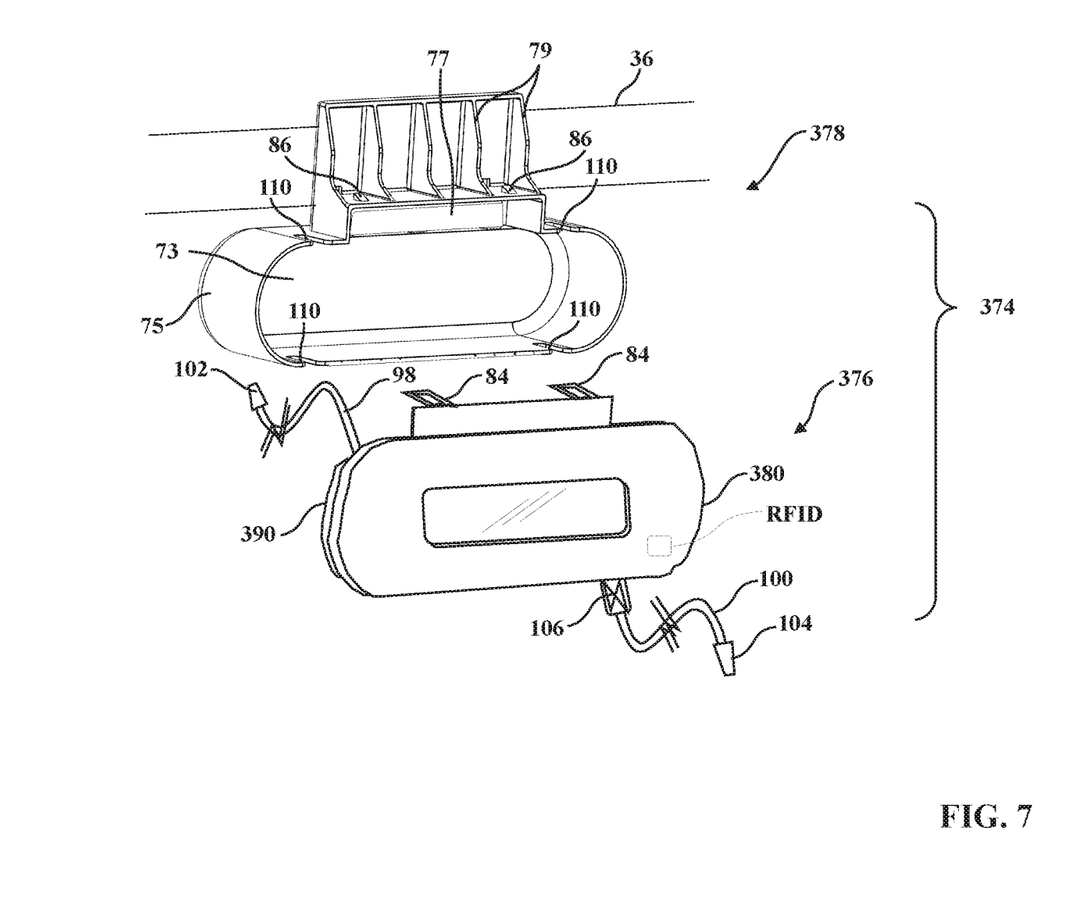
FIG. 7 is an exploded view of the urine collection system with yet another alternative container.

Referring to FIG. 7, yet another alternative container 376 is shown. In this version, the container 76 previously described above is combined with the housing lid 80 to form an integrated assembly. Thus, the container 376 comprises a flaccid portion 390, which comprises all the components of the container 76, except for the openings 97. A lid portion 380 comprises all the features of the housing lid 80 described above, except that the lid portion 380 is not configured to be pivotally connected to the housing base 78 by the pivot pins 82. Instead, the lid portion 380 is configured to be releasably coupled to the housing base 378 using the latches 84 to engage the catches 86. The flaccid portion 390 may be attached to the lid portion 380 by fasteners, adhesive, welding, or the like. Additional latches and catches may be employed to better hold the lid portion 380 onto the housing base 378. Other releasable coupling mechanisms may also be employed to hold the lid portion 380 on the housing base 378. During use, the flaccid portion 390 is at least partially enclosed inside the housing 374 between the bottom wall 73 and the lid portion 380.

As shown in FIG. 7, window openings W may be present in the lid portion 380 to view filling of the flaccid portion 390 to determine when the container 376 is full. The tubes 98, 100 may be connected to the flaccid portion 390 in the same manner previously described with respect to the container 76.

The containers 76, 176, 276, 376 may be disposable, reusable, capable of being sterilized, combinations thereof, and the like. Similarly, the housing 74 may be disposable, reusable, capable of being sterilized, combinations thereof, and the like. In one non-limiting example, the housing 74 is reusable and may be removed from time-to-time for autoclave sterilization. The containers 76 and 176 are disposable, while the containers 276, 376 are configured to be reusable and capable of being sterilized for additional uses.

Figure 8:
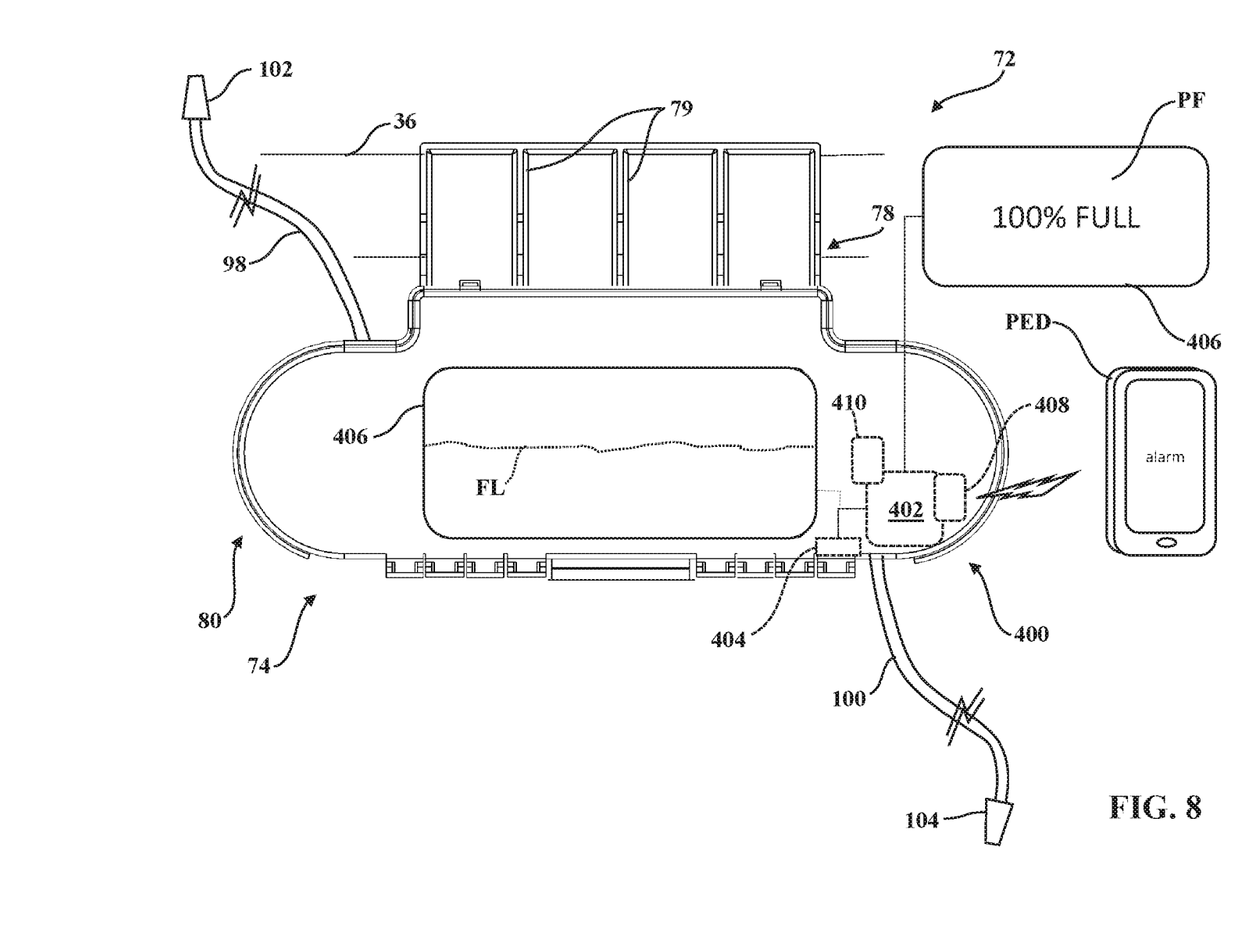
FIG. 8 is a front view of an alternative urine collection system with electronic notification.

FIG. 8 illustrates a control system 400 of the urine collection system 72. The control system 400 comprises a controller 402, one or more sensors 404 coupled to the controller 402, one or more displays 406 coupled to the controller 402, and a communications module 408 coupled to the controller 402. The controller 402 is configured to transmit and/or receive input/output signals to/from the various components shown in FIG. 8. The controller 402 may communicate with these components via wired or wireless connections to control the various components shown, to control other components not represented in FIG. 8, and/or to otherwise carry out the functions described herein.

The controller 402 comprises one or more microprocessors for processing instructions or for processing algorithms stored in memory to carry out the functions described herein. Additionally or alternatively, the controller 402 may comprise one or more microcontrollers, subcontrollers, field programmable gate arrays, systems on a chip, discrete circuitry, and/or other suitable hardware, software, or firmware that is capable of carrying out the functions described herein. The controller 402 may be carried on-board the patient support apparatus 30, the housing 74, or may be remotely located. In one embodiment, the controller 402 is mounted to the housing base 78, but can be mounted in any suitable location. Memory may be any memory suitable for storage of data and computer-readable instructions. For example, the memory may be a local memory, an external memory, or a cloud-based memory embodied as random access memory (RAM), non-volatile RAM (NVRAM), flash memory, or any other suitable form of memory. Power to the various components may be provided by a battery power supply and/or external power source. In some versions, the urine collection system 72 lacks any electronic components.

In one embodiment, the sensors 404 comprise one or more load cells, pressure sensors, strain gauges, or the like that are configured to monitor a weight of the container 76, 176, 276, 376. The one or more sensors 404 thereby generated load signals that the controller 402 interprets to determine changes in weight of the container 76, 176, 276, and 376. These changes in weight can then be correlated with fullness of the container 76, 176, 276, 376 and can be used to generate alarms when the container 76, 176, 276, 376 is full or nearly full so that a caregiver can replace the container as needed.

The display 406 may be coupled to the controller 402 so that the controller 402 can transmit output signals to the display 406 to display information associated with the urine collection system 72. The display 406 can be used to display graphical information, text, or other indicia associated with use of the urine collection system 72, such as percent full PF (as shown), a graphic of a liquid fill line FL (as shown), estimated time until a new container 76, 176, 276, 376 will be needed based on trend data associated with the current use of the urine collection system 72, and the like. The communications module 408 is coupled to the controller 402 and can be used to transmit/receive signals to/from portable electronic devices PED to transmit alarms to caregivers, etc.

An RFID reader 410 may also be coupled to the controller 402 and configured to read signals from radio frequency identification (RFID) tags on the containers 76, 176, 276, 376, which may be used to verify that appropriate containers are being used, to identify the type of containers being used, to identify a size/volume of container being used, and the like. For example, unique identifiers may be read off the RFID tags by the RFID reader 410 to determine the maximum volume of liquid that can be stored in that specific container (e.g., via a look-up table stored in memory in the controller 402) or the RFID tag may indicate the maximum volume of liquid that can be stored, which can then be used by the controller 402 to provide accurate information with respect to current liquid level/fullness of the container. The RFID tags may also be useful to reset measurements being made by the controller 402, i.e., when a new RFID tag is sensed, the measurements are reset to zero.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support apparatus comprising:
a support structure including a base arranged for movement over floor surfaces and extending in a longitudinal direction between a head end and a foot end, a support frame configured to be lifted and lowered in a vertical direction relative to the base, and a patient support deck disposed on the support frame and having a patient support surface; and
a housing defining a storage space for receiving an expandable urine collection container, the housing comprising a rigid housing base including a catch and carried by the support frame of the support structure for concurrent vertical movement relative to the base, and a lid movable relative to the rigid housing base and including a latch for engaging the catch of the rigid housing base to releasably lock the housing in a closed configuration, the housing configured to support the expandable urine collection container in the storage space in the closed configuration;
wherein the rigid housing base comprises a bottom wall and a peripheral wall extending from the bottom wall so that the rigid housing base has a side opening facing away from the patient support apparatus in a lateral direction when the lid is opened from the closed configuration; and
wherein the lid is pivotally connected to the rigid housing base at a location arranged vertically below the catch so that the lid falls open under gravity when the latch is released from the catch.

2. The patient support apparatus of claim 1, wherein the housing has a coupler for engaging the expandable urine collection container when the expandable urine collection container is inserted in the storage space.

3. The patient support apparatus of claim 2, wherein the coupler comprises a retainer for receiving the expandable urine collection container.

4. The patient support apparatus of claim 3, wherein the retainer comprises a hook.

5. The patient support apparatus of claim 1, comprising one or more line managers to route one or more tubes connected to the expandable urine collection container from inside the storage space to outside the storage space.

6. The patient support apparatus of claim 5, wherein the one or more line managers comprise one or more notches formed in the housing and sized to receive the one or more tubes connected to the expandable urine collection container.

7. The patient support apparatus of claim 1, wherein the housing comprises a window for viewing the expandable urine collection container inside the storage space when closed by the lid.

8. The patient support apparatus of claim 1, wherein the lid is pivotally connected to the rigid housing base.

9. The patient support apparatus of claim 8, comprising one or more pivot pins pivotally connecting the lid to the rigid housing base.

10. The patient support apparatus of claim 1, wherein the rigid housing base and the lid are formed of plastic.

11. The patient support apparatus of claim 1, wherein the peripheral wall of the rigid housing base is shaped to define the storage space with:
a vertical dimension extending in the vertical direction; and
a longitudinal dimension extending in the longitudinal direction, the longitudinal dimension being larger than the vertical dimension.

12. The patient support apparatus of claim 11, wherein the longitudinal dimension is at least twice as large as the vertical dimension.

13. The patient support apparatus of claim 12, wherein the peripheral wall of the rigid housing base is further shaped to define the storage space with a lateral dimension extending in the lateral direction between the bottom wall and the side opening, the lateral dimension being smaller than the longitudinal dimension.

14. The patient support apparatus of claim 13, wherein the longitudinal dimension is at least twice as large as the lateral dimension.

15. A patient support apparatus comprising:
a support structure including a base arranged for movement over floor surfaces and extending in a longitudinal direction between a head end and a foot end, a support frame configured to be lifted and lowered in a vertical direction relative to the base, and a patient support deck disposed on the support frame and having a patient support surface; and
a housing defining a storage space for receiving an expandable urine collection container, the housing comprising a rigid housing base carried by the support frame of the support structure for concurrent vertical movement relative to the base, and a lid movable relative to the rigid housing base for engaging the rigid housing base in a closed configuration, the housing configured to support the expandable urine collection container in the storage space in the closed configuration;
wherein the rigid housing base comprises a bottom wall and a peripheral wall extending from the bottom wall so that the rigid housing base has a side opening facing away from the patient support apparatus in a lateral direction when the lid is opened from the closed configuration;
wherein the rigid housing base comprises a catch and the lid comprises a latch for engaging the catch to releasably lock the housing in the closed configuration;
wherein the lid is pivotally connected to the rigid housing base at a location arranged vertically below the catch so that the lid falls open under gravity when the latch is released from the catch; and
wherein the peripheral wall of the rigid housing base is shaped to define the storage space with:
a vertical dimension extending in the vertical direction; and a longitudinal dimension extending in the longitudinal direction, the longitudinal dimension being larger than the vertical dimension.

16. The patient support apparatus of claim 15, wherein the peripheral wall of the rigid housing base is further shaped to define the storage space with a lateral dimension extending in the lateral direction between the bottom wall and the side opening, the lateral dimension being smaller than the longitudinal dimension.

* * * * *